United States Patent

Shamshoum et al.

[11] Patent Number: 5,336,824
[45] Date of Patent: Aug. 9, 1994

[54] MORDENITE CATALYSTS IN TOLUENE SYNTHESIS

[75] Inventors: Edwar S. Shamshoum; Ashim K. Ghosh, both of Clear Lake, Tex.

[73] Assignee: Fina Technology, Inc., Dallas, Tex.

[21] Appl. No.: 11,029

[22] Filed: Jan. 29, 1993

[51] Int. Cl.⁵ .......................... C07C 2/66; C07C 5/52
[52] U.S. Cl. .................................. 585/475; 585/446; 585/467
[58] Field of Search ............... 585/475, 446, 467, 470, 585/471, 514, 323

[56] References Cited

U.S. PATENT DOCUMENTS

| | | | |
|---|---|---|---|
| 3,476,821 | 11/1969 | Brandenburg et al. | 260/672 |
| 4,861,935 | 8/1989 | Bakas et al. | 585/474 |
| 4,956,511 | 9/1990 | Butler et al. | 585/475 |
| 5,177,280 | 1/1993 | Juguin et al. | 585/323 |

*Primary Examiner*—Anthony McFarland
*Assistant Examiner*—P. Achutamurthy
*Attorney, Agent, or Firm*—Betty M. Ellsworth; M. Norwood Cheairs

[57] ABSTRACT

In accordance with the the present invention, there is provided a process for the conversion of aromatic hydrocarbons including benzene to hydrocarbon components comprising primarily toluene. According to the invention, a catalyst reaction zone is established having a metal-loaded mordenite catalyst. A mixed feedstock of aromatic hydrocarbons, including benzene, xylene(s) and, optionally, ethylbenzene is introduced into the reaction zone and hydrogen is used as a cofeed to provide a reductive environment. The feedstock is contacted with the metal-loaded mordenite catalyst and the conversion of the aromatic hydrocarbon components is conducted under temperature and pressure conditions sufficient to effect the conversion of the feedstock to hydrocarbon components containing primarily toluene. Finally, the conversion product containing primarily toluene is recovered from the reaction zone.

13 Claims, 8 Drawing Sheets

MORDENITE CATALYSTS IN TOLUENE SYNTHESIS

TECHNICAL FIELD OF THE INVENTION

This invention relates to the conversion of mixed alkylaromatic feedstreams and more particularly to the conversion of a feedstock comprising benzene, xylene and, optionally, ethylbenzene, to hydrocarbon components comprising primarily toluene by employing a metal-loaded mordenite zeolite catalyst.

BACKGROUND OF THE INVENTION

Processes for the disproportionation of toluene to produce benzene are well-known in industrial applications. Recently, however, the economic desirability of producing benzene has come under question. The effects of recent legislation, including the Clean Air Act, limit benzene levels in gasoline pools, which, in turn, may reduce the economic incentive to produce benzene. Consequently, these effects may cause an excessive amount of benzene in the market which may result in a decrease in the price of benzene.

In preparation for the regulations concerning a reformulated gasoline pool, including dropping the aromatic levels and removing benzene and xylene, a catalytic process using a mordenite catalyst has been developed to convert benzene and $C_8$ aromatics, such as xylene and ethylbenzene, to toluene. The toluene can be added to the gasoline pool for octane boost. This process involves transfer of the alkyl group between xylene(s) and benzene, producing toluene as a major product and other alkylated hydrocarbons (C9+).

The conversion of a mixed alkylaromatic feed comprising benzene, xylene(s) and, optionally, ethylbenzene to form toluene may be practiced in accordance with the following reaction:

As carried out in the instant invention, reaction (1) employs a metal-loaded mordenite zeolite catalyst. Ethylbenzene may be employed as an optional feedstock component.

Mordenite is one of a number of molecular sieve catalysts useful in the conversion of alkylaromatic compounds. Mordenite is a crystalline aluminosilicate zeolite exhibiting a network of silicon and aluminum atoms interlinked by oxygen atoms within the crystalline structure. For a general description of mordenite catalysts, reference is made to Kirk-Othmer, *Encyclopedia of Chemical Technology*, 3rd Edition, 1981, under the heading "Molecular Sieves", Vol 15, pages 638–643.

Mordenite as found in nature, or as synthesized to replicate the naturally occurring zeolite, typically exhibits a relatively low silica to alumina mole ratio of about 10 or less. Also known are "aluminum-deficient" mordenite catalysts exhibiting silica to alumina ratios between 10 and 100, which may be prepared by direct synthesis as disclosed in U.S. Pat. No. 3,436,174 to Sand or by acid extraction of a more conventionally prepared mordenite as disclosed in U.S. Pat. No. 3,480,539 to Voorhies, et. al. Both the typical and the aluminum deficient mordenites are known to be useful in toluene disproportionation reactions.

It is also a common practice to promote (or load) an aluminum deficient mordenite catalyst with a catalytically active metallic component. For example, U.S. Pat. No. 3,476,821 to Brandenburg et al. discloses disproportionation reactions employing mordenite catalysts having silica/alumina ratios within the range of 10–100 and preferably within the range of about 20–60. The mordenites are modified by the inclusion of a sulfided metal selected from the Group VIII metals. The metal may be included in the mordenite by well known ion exchange or impregnation techniques. The metal promoters substantially increase activity and catalyst life, as indicated by runs extending over several hours or days.

Other patents, such as U.S. Pat. No. 4,956,511 to Butler, U.S. Pat. No. 4,761,514 to Menard, U.S. Pat. No. 3,562,345 to Mitsthe and U.S. Pat. No. 3,677,973 to Mitsthe et al., disclose the use of molecular sieves such as mordenite catalysts in the disproportionation of toluene, and each of the entire disclosures of the above-referenced patents are incorporated herein by reference.

While metal-promoted mordenite catalysts may typically be used in toluene disproportionation processes, it has become desirable to employ these catalysts in a reverse toluene disproportionation process, i.e., toluene synthesis. Given the facts that (1) gasoline specifications will limit benzene levels and (2) toluene could be effectively used as a substitute for benzene, a benzene surplus may result causing the economic value of toluene to rise. It has therefore become desirable to develop a process for the conversion of surplus benzene and xylenes to toluene.

SUMMARY OF THE INVENTION

In accordance with the present invention, there is provided a process for the conversion of aromatic hydrocarbons including benzene to hydrocarbon components comprising primarily toluene.

According to one aspect of the invention, a catalyst reaction zone is established having a metal-loaded mordenite zeolite catalyst. A mixed feedstock of aromatic hydrocarbons, including benzene, is introduced into the reaction zone at a rate sufficient to produce a liquid hourly space velocity (LHSV) of approximately 2 hr$^{-1}$. Hydrogen is introduced as a cofeed into the reaction zone to provide a reductive environment. The feedstock is then contacted with the metal-loaded mordenite catalyst and the conversion of the aromatic hydrocarbon components is conducted under temperature and pressure conditions sufficient to effect the conversion of the feedstock to hydrocarbon components containing primarily toluene. Finally, the conversion product containing primarily toluene is recovered from the reaction zone.

The metal-loaded mordenite may include nickel, gallium, zinc, palladium, copper, chromium or such combinations as nickel and gallium, and nickel and zinc. To effect a conversion, the temperature of the reaction zone is maintained within the range of 250° to 450° C. The pressure of the reaction zone is operated at a pressure within the range of 500 to 700 psig.

BRIEF DESCRIPTION OF THE FIGURES

Further aspects of the invention and their advantages will be discerned when one refers to the following detailed description as taken in conjunction with the drawings, in which.

DETAILED DESCRIPTION OF THE INVENTION

The process of toluene synthesis, according to the present invention, involves a novel application of a metal-promoted mordenite zeolite catalyst in the conversion of aromatic hydrocarbons including benzene to produce hydrocarbon components comprising primarily toluene. The metal-promoted mordenite catalysts employed in the present invention are modified by the inclusion of nickel, gallium and zinc, and combinations of nickel and gallium, and nickel and zinc. The invention may also be carried out using metal-promoted mordenite catalysts modified by the inclusion of palladium, copper or chromium.

Eight metal-promoted mordenite catalysts (Catalysts I–VIII, described infra) were tested for the conversion of the aromatic compounds. Catalyst I was modified by the inclusion of nickel in the amount of approximately 1.4 weight percent. As used in the claimed process, nickel can be incorporated into the mordenite by any suitable technique including well known impregnation and exchange procedures. A nickel mordenite catalyst suitable for use as Catalyst I may be obtained from Universal Oil Products (UOP) of Des Plaines, Ill. Catalysts II–VIII included synthesized mordenite powder samples ion-exchanged with ammonium ions, followed by the incorporation (also by ion-exchange) of nickel, zinc and gallium (as subsequently described) into the mordenite zeolite. The zinc-dealuminated mordenite of Catalyst VIII was prepared by first dealuminating (by acid extraction) and then ion-exchanging the mordenite zeolite. All mordenite samples were then extruded with 20% alumina as a binder and calcined at 530° C. These techniques used for preparing the mordenite samples are well known in the art.

The mordenite catalyst employed in the present invention is preferably a moderately to highly aluminum deficient mordenite catalyst having a silica to alumina mole ratio within the range of 10 to 60. Catalysts I–VII had a silica to alumina mole ratio (SAR) of approximately 18. Catalyst VIII had an SAR of approximately 59. Aluminum deficient mordenite catalysts and processes for preparing same are well known in the art.

The eight catalysts tested for the conversion of aromatic hydrocarbons, including benzene, xylene and ethylbenzene, are described below in TABLE 1.

TABLE 1

| Mordenite Catalysts. | |
|---|---|
| Catalyst Designation | Description |
| I Ni/Mordenite (Ni = 1.4%) | Commercial Catalyst |
| II Ni(0.5%)/Mordenite (SAR = 18) | Prepared by ion-exchange method. |
| III Ni(0.3%)/Zn(0.3%)/Mordenite (SAR = 18) | Prepared in the lab by simultaneous ion-exchange method. |
| IV Ni(1.4%)/Zn(0.5%)/Mordenite (SAR = 18) | Prepared in the lab by simultaneous ion-exchange method. |
| V Zn(0.5%)/Mordenite (SAR = 17) | Prepared in the lab by ion-exchange method. |
| VI Ga(0.5%)/Mordenite (SAR = 18) | Prepared in the lab by ion-exchange method. |
| VII Ni(0.4%)/Ga(0.4%)/Mordenite (SAR = 18) | Prepared in the lab by ion-exchange method. |
| VIII Zn(0.5%)/Deal-Mordenite (SAR = 59) | Prepared by acid dealumination followed by ion-exchange method. |

The experimental work described as follows is provided to illustrate the invention in accordance with the principles of the invention, but is not to be construed as limiting the invention.

In preparation for the disclosed process, a known volume of approximately 15 ml. of precalcined metal-promoted mordenite catalyst was loaded into a microreactor. Hydrogen was introduced as a cofeed into the reaction zone to establish a reductive environment, as the catalyst dried in the reactor at temperatures between 200° and 250° C. While the reverse disproportionation reaction (1) does not involve chemical consumption of hydrogen, the use of a hydrogen cofeed is generally considered to prolong the useful life of the catalyst. Such use of hydrogen as a preflush gas is well known in the art. Next, a premixed feed of aromatic hydrocarbons, including benzene, xylene(s) and ethylbenzene, was introduced in a down-flow mode at approximately 250° C., at a desired rate to give a feedstock liquid hourly space velocity (LHSV) of approximately 2 $hr^{-1}$. Hydrogen was again used as a cofeed, preferably adjusted to give a hydrogen/feed mole ratio of between 3 and 4. The reactor temperature was gradually increased from about 250° up to temperatures between 300° and 450° C., preferably within the range of 300°–400° C. Pressures were within the range of 500 to 700 psig.

Both the liquid and gas effluent samples were analyzed to calculate percent conversion of the aromatics and selectivities to the conversion products. The percent conversion of each of the aromatic hydrocarbons and the percent selectivity to toluene were calculated using the following equations:

% Conversion of $X = [(Wt\% \ X_F - Wt\% \ X_E)/Wt\% \ X_F] \times 100$

% Selectivity of $X = [(Wt\% \ X_E - Wt\% \ X_F)/\%$ Conversion of the aromatics$] \times 100$ where, in each of the above equations, Wt% $X_F$=Weight percent of X in feed; and Wt% $X_E$=Weight percent of X in effluent.

Catalyst I, as described supra, was used as a reference catalyst to determine the optimal feedstock mixture of benzene, xylene(s) and ethylbenzene (including whether ethylbenzene was required in the feedstock). The following four feed mixtures were used:

FEED 1: Benzene 49.3 wt %, Xylenes 44.5 wt %, EB 5.8 wt %,

FEED 2: Benzene 53.2 wt %, Xylenes 34.8 wt %, EB 4.8 wt %,

FEED 3: Benzene 39.8 wt %, Xylenes 22.3 wt %, EB 3.2 wt %,

FEED 4: Benzene 39.8 wt %, Xylenes 52.9 wt %, EB 0.7 wt %.

Figure 1:
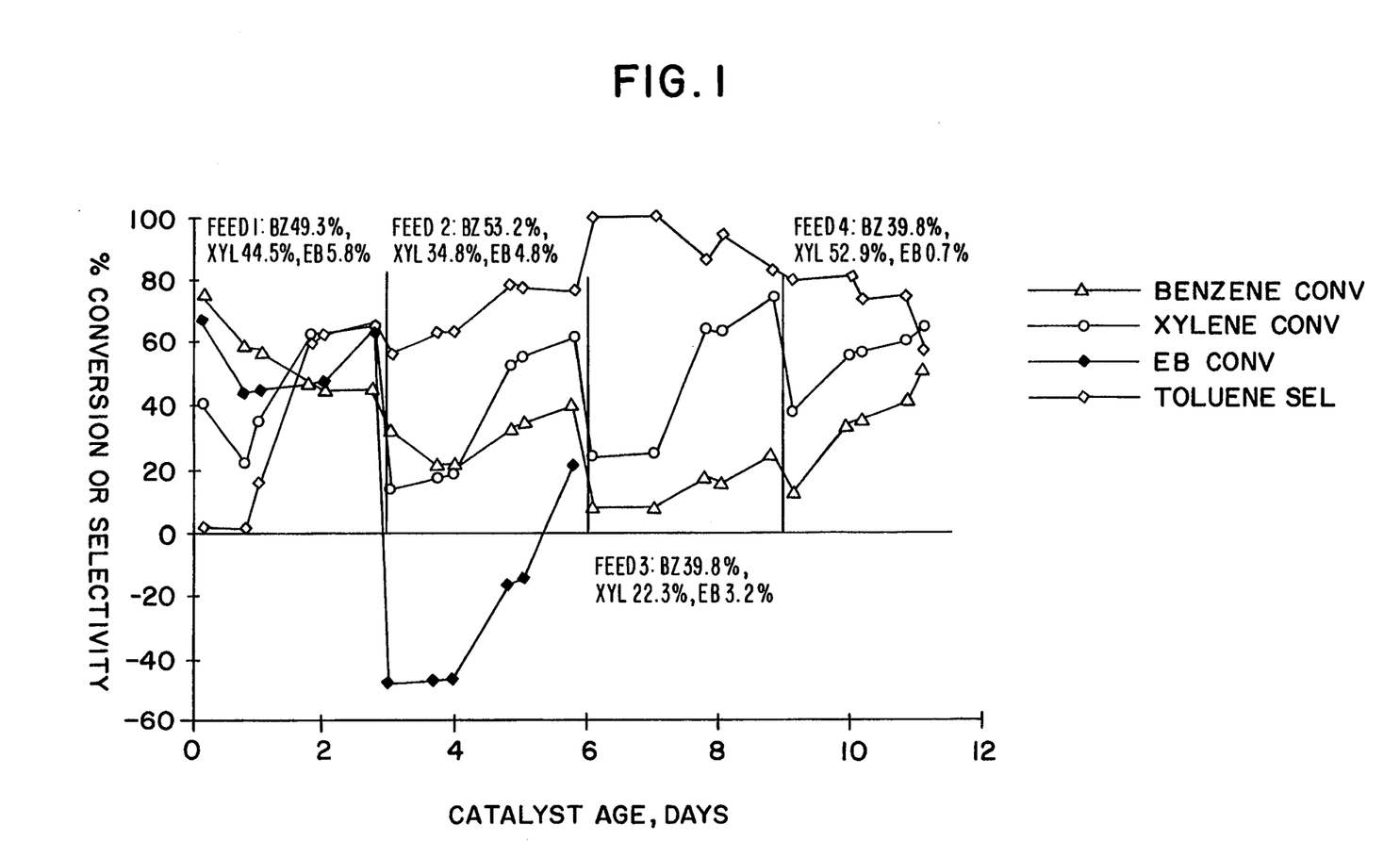
FIG. 1 is a graph illustrating the relationship between the conversion of benzene, xylenes and ethylbenzene and selectively to toluene as a function of catalyst age over a nickel/mordenite catalyst (Catalyst I)
Figure 2:
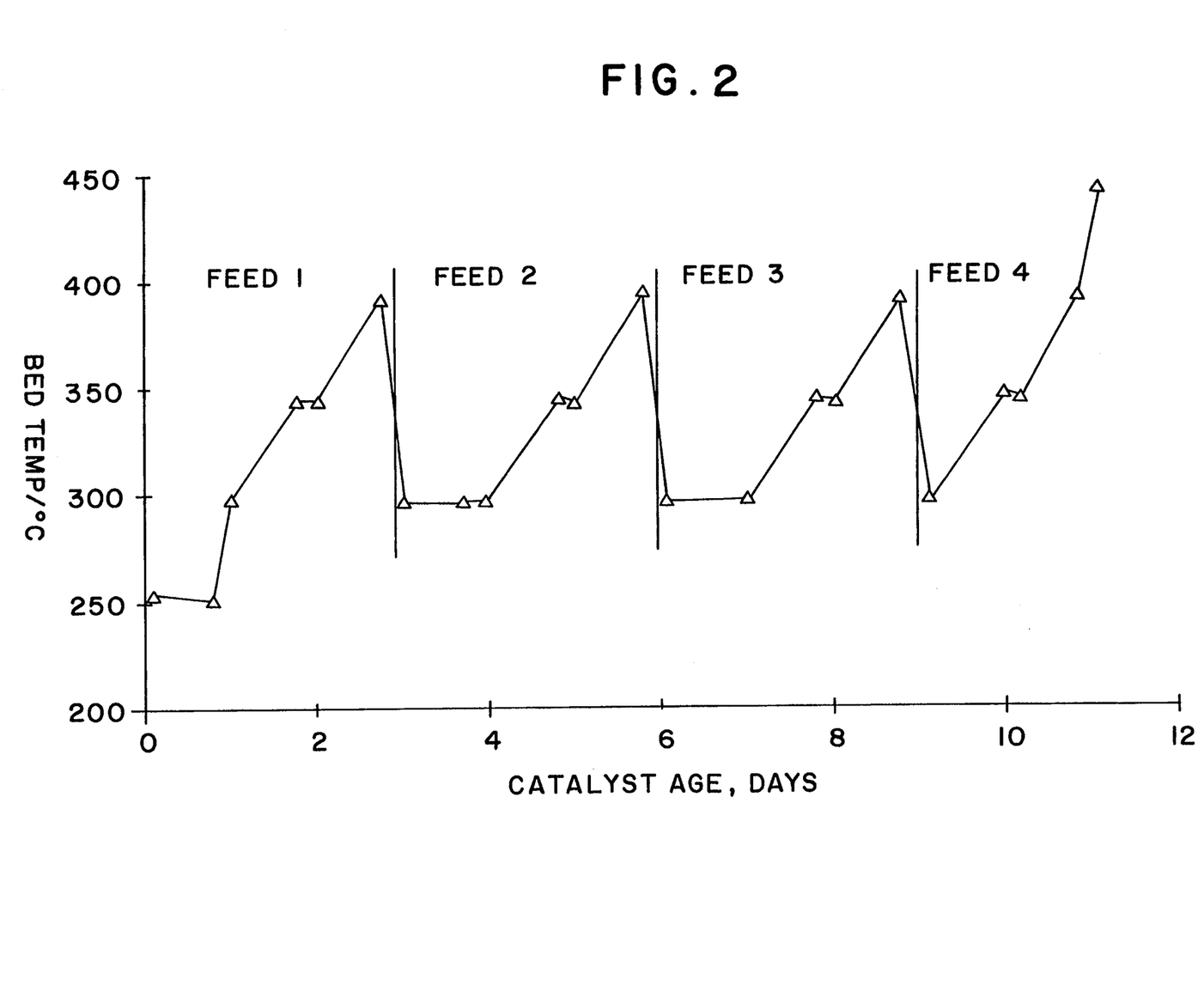
FIG. 2 is a graph illustrating the relationship between the temperature of the reactor bed as a function of the catalyst age, also over a nickel/mordenite catalyst (Catalyst I)

Catalyst I was also used to provide a general idea of the manner in which the reactor bed temperature affected conversion activity and selectivity to toluene. Turning to the drawings, FIG. 1 depicts conversion activity and selectivity to toluene for each of the four feed mixtures. FIG. 2 depicts the corresponding reactor bed temperatures for each of the mixtures 1–4 described supra. FIGS. 1 and 2, when viewed together, illustrate the effect of feed content and reactor bed temperature on the conversion of aromatics and the selectivity to toluene over Catalyst I.

Due to the occurrence of concomitant reactions, a greater percentage of a component was sometimes observed in the product effluent than in the feedstock mixture, resulting in a negative percent conversion. Specifically, this was observed in feed mixtures 2–4 with respect to ethylbenzene conversion. As depicted, ethylbenzene conversion in feed mixture 1 approximated 40–65%. However, as the ethylbenzene concentration was lowered in feed mixture 2, a negative conversion was observed at temperatures below around 350° C. (Refer to FIG. 2 to observe the reactor bed temperatures corresponding to each feed mixture.) Ethylbenzene conversion in feed mixtures 3 and 4 exhibited much greater negative values, up to 500% (not illustrated). Consequently, from FIG. 1 it can be observed that ethylbenzene conversion was apparently dependent on its concentration in the feed mixture.

The concentration of benzene in each of the feed mixtures 1–4 ranged within 39–55 weight percent. Generally (except for feed mixture 1), benzene conversion increased with an increase in temperature. The concentration of total xylenes ranged between 22–53 weight percent for all feed mixtures. In each case, total xylene conversion also increased with an increase in temperature. (See FIGS. 1 and 2.) Unlike ethylbenzene, the concentration of benzene and total xylenes did not appear to affect their respective conversion activities.

After completing the conversion selectivity and reactor bed temperature tests employing Catalyst I, each of the Catalysts I–VIII, were tested using a feedstock mixture having a benzene:xylene:ethylbenzene ratio of approximately 5:4:1. In the case of the zinc dealuminated mordenite catalyst (Catalyst VIII), a ratio of 5:4:0.5 was used due to the presence of a small amount of heavy aromatics (C9+) in the feed.

Listed below are test results for each of the Catalysts I through VIII.

TABLE 2

Conversion Activities and Selectivities over Mordenite Catalysts.

Figure 3:
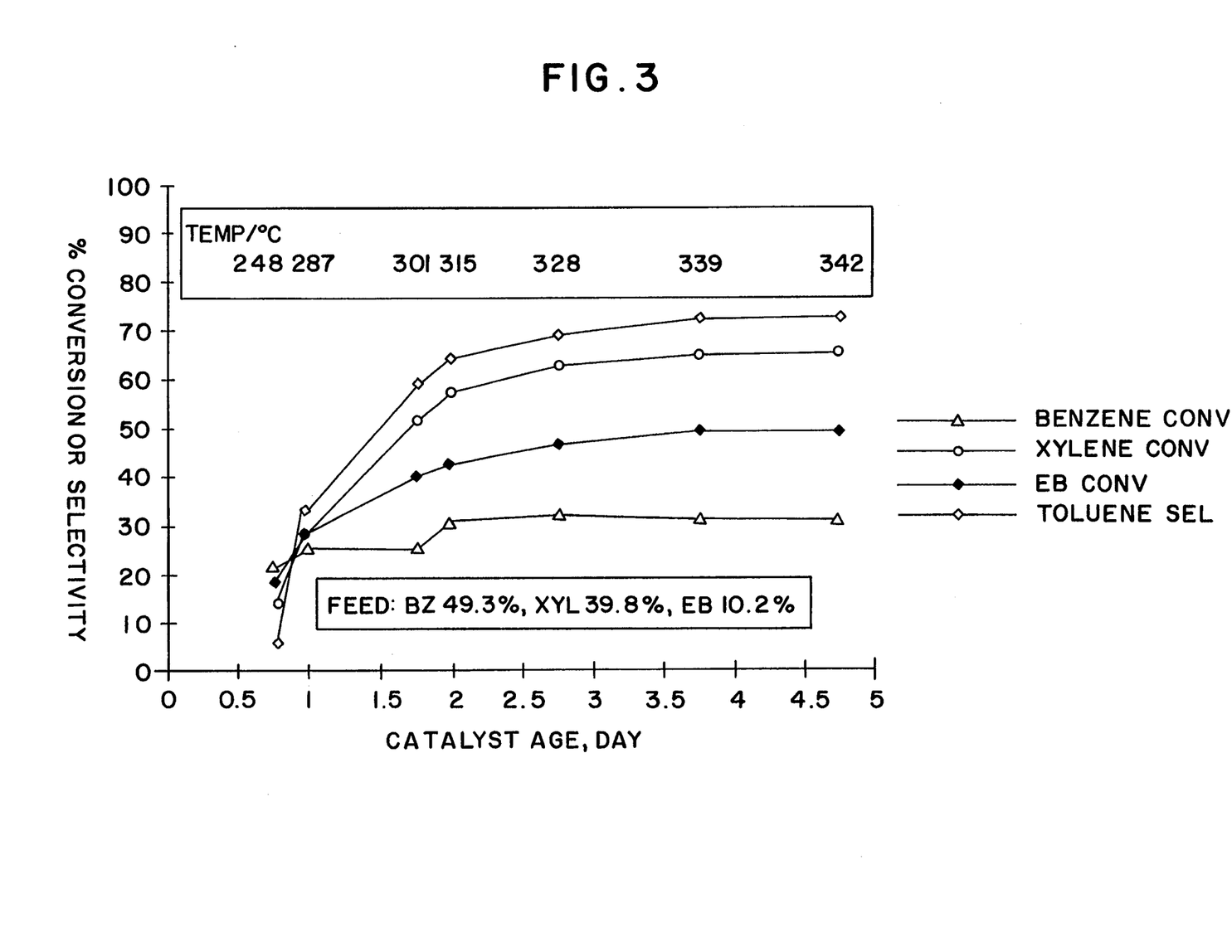
FIG. 3 is a graph depicting the relationship of the conversion of benzene, xylenes and ethylbenzene and the selectivity to toluene as a function of catalyst age over a nickel/mordenite catalyst (Catalyst I)

CATALYST I - Ni/Mordenite (Ni = 1.4%) (See FIGS. 1, 2, 3.)

| Temperature (°C.) | 248 | 287 | 301 | 328 | 342 | 344 |
|---|---|---|---|---|---|---|
| Conversion Weight % | | | | | | |
| Benzene Conv. | 20.5 | 25.3 | 25.2 | 32.0 | 31.0 | 36.3 |
| Total Xylenes Conv. | 13.6 | 28.1 | 51.5 | 62.4 | 64.8 | 69.2 |
| Ethylbenzene Conv. | 19.0 | 28.2 | 40.1 | 46.5 | 49.2 | 60.1 |
| Selectivity, Weight %: | | | | | | |
| Toluene | 5.6 | 33.1 | 58.8 | 68.7 | 72.3 | 51.1 |

Figure 4:
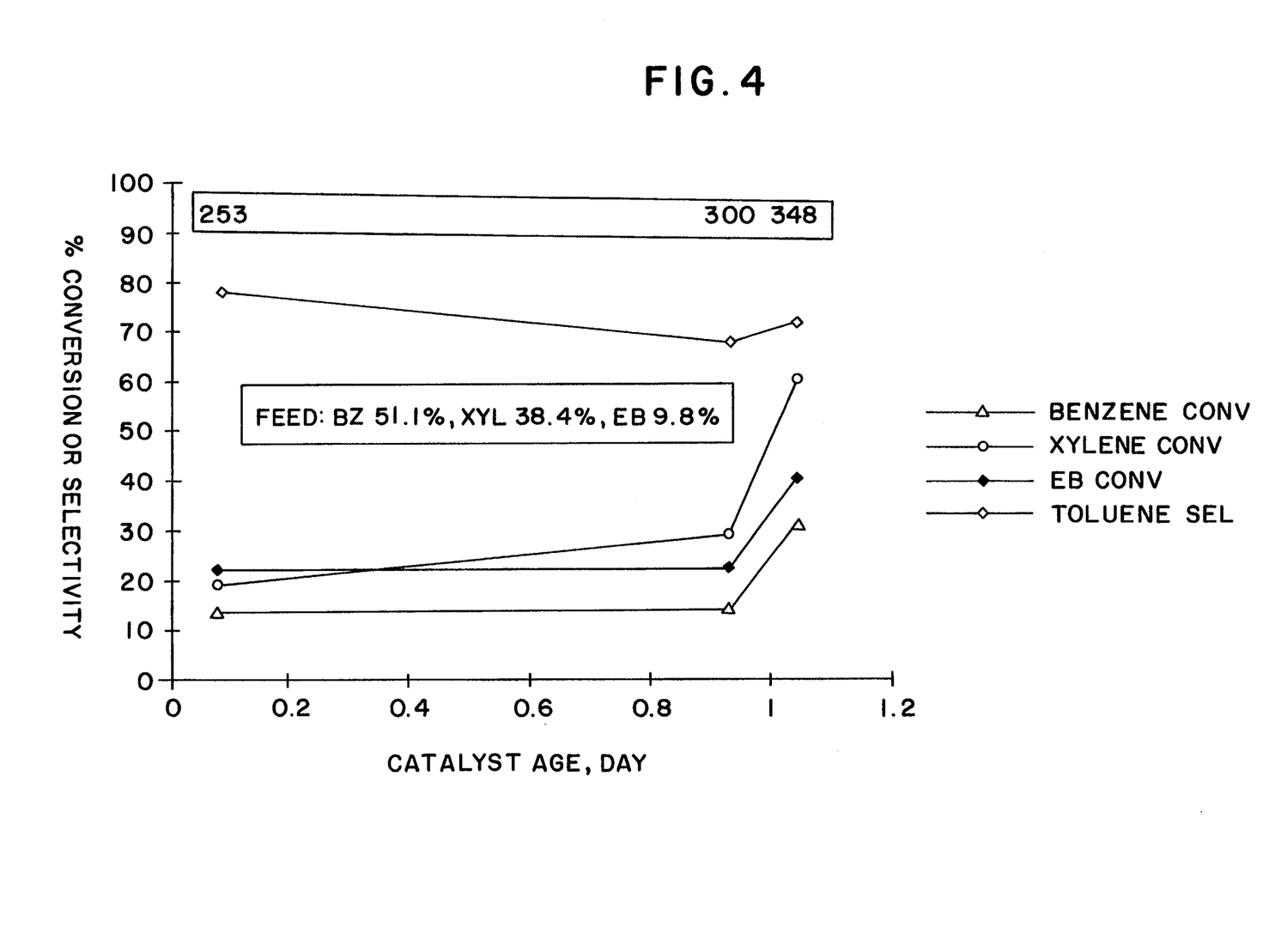
FIG. 4 is a graph depicting the relationship of the conversion of benzene, xylenes and ethylbenzene and the selectivity to toluene as a function of catalyst age over a second nickel/mordenite catalyst (Catalyst II)

CATALYST II - Ni(0.5%)/Mordenite (See FIG. 4.)

| Temperature °C. | 253 | 300.2 | 348.2 |
|---|---|---|---|
| Conversion, Weight % | | | |
| Benzene Conv. | 13.5 | 14.0 | 31.1 |
| Total Xylenes Conv. | 19.2 | 29.2 | 60.2 |
| Ethylbenzene Conv. | 22.3 | 22.7 | 40.3 |
| Selectivity, Weight % | | | |
| Toluene | 78.0 | 67.7 | 71.5 |

Figure 5:
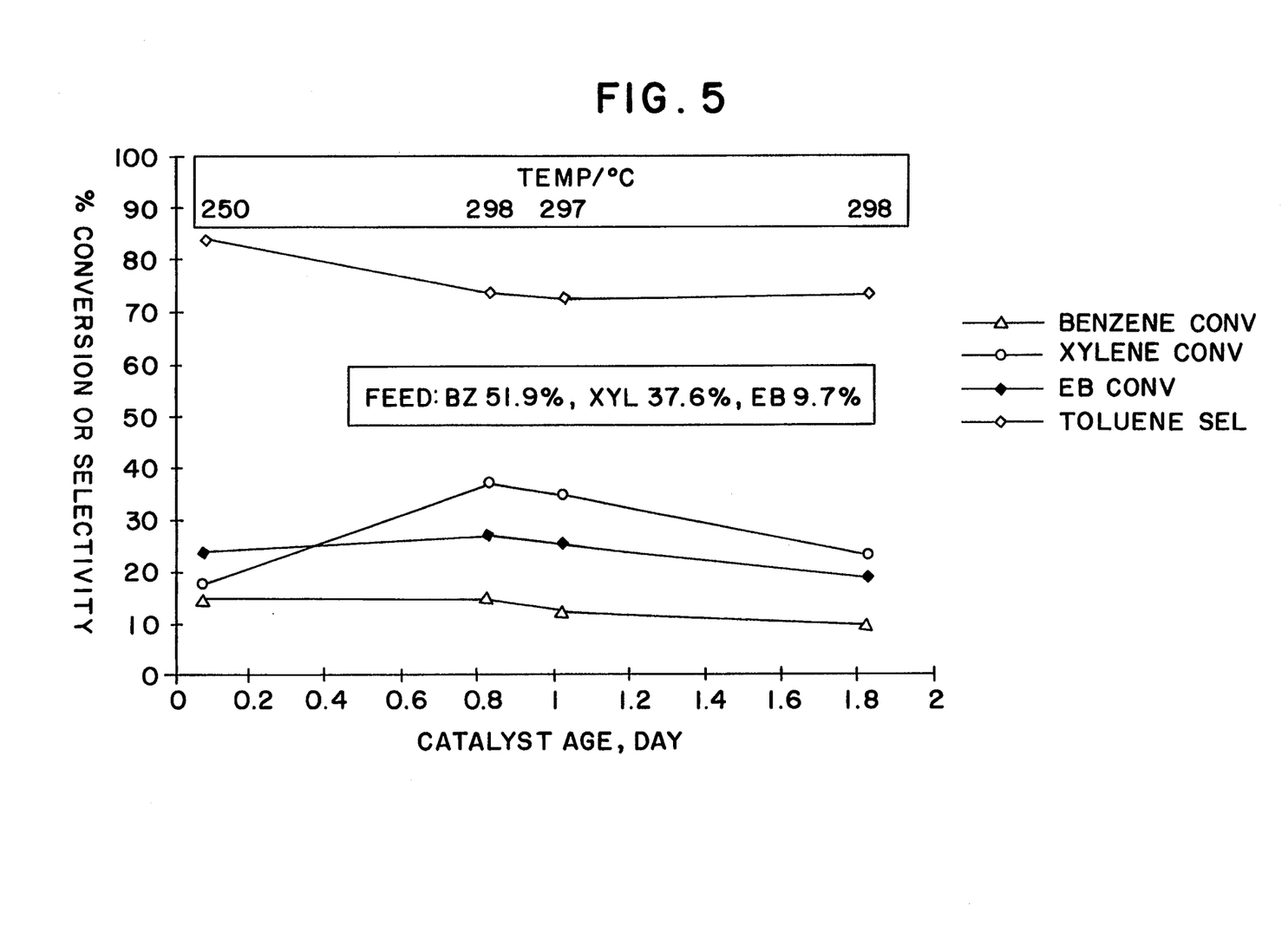
FIGS. 5 and 6 are graphs depicting the relationship of the conversion of benzene, xylenes and ethylbenzene, and selectivity to toluene as a function of catalyst age over two types nickel/zinc/mordenite catalyst (Catalyst III and IV)

CATALYST III - Ni(0.3%)/Zn(0.3%)/Mordenite (See FIG. 5.)

| Temperature °C. | 250 | 298 | 296.8 | 298 |
|---|---|---|---|---|
| Conversion, Weight % | | | | |
| Benzene Conv. | 14.6 | 14.6 | 12.4 | 9.4 |
| Total Xylenes Conv. | 17.4 | 37.1 | 34.8 | 22.8 |
| Ethylbenzene Conv. | 23.6 | 26.9 | 25.4 | 18.6 |
| Selectivity, Weight % | | | | |
| Toluene | 83.7 | 75.8 | 72.6 | 75.1 |

Figure 6:
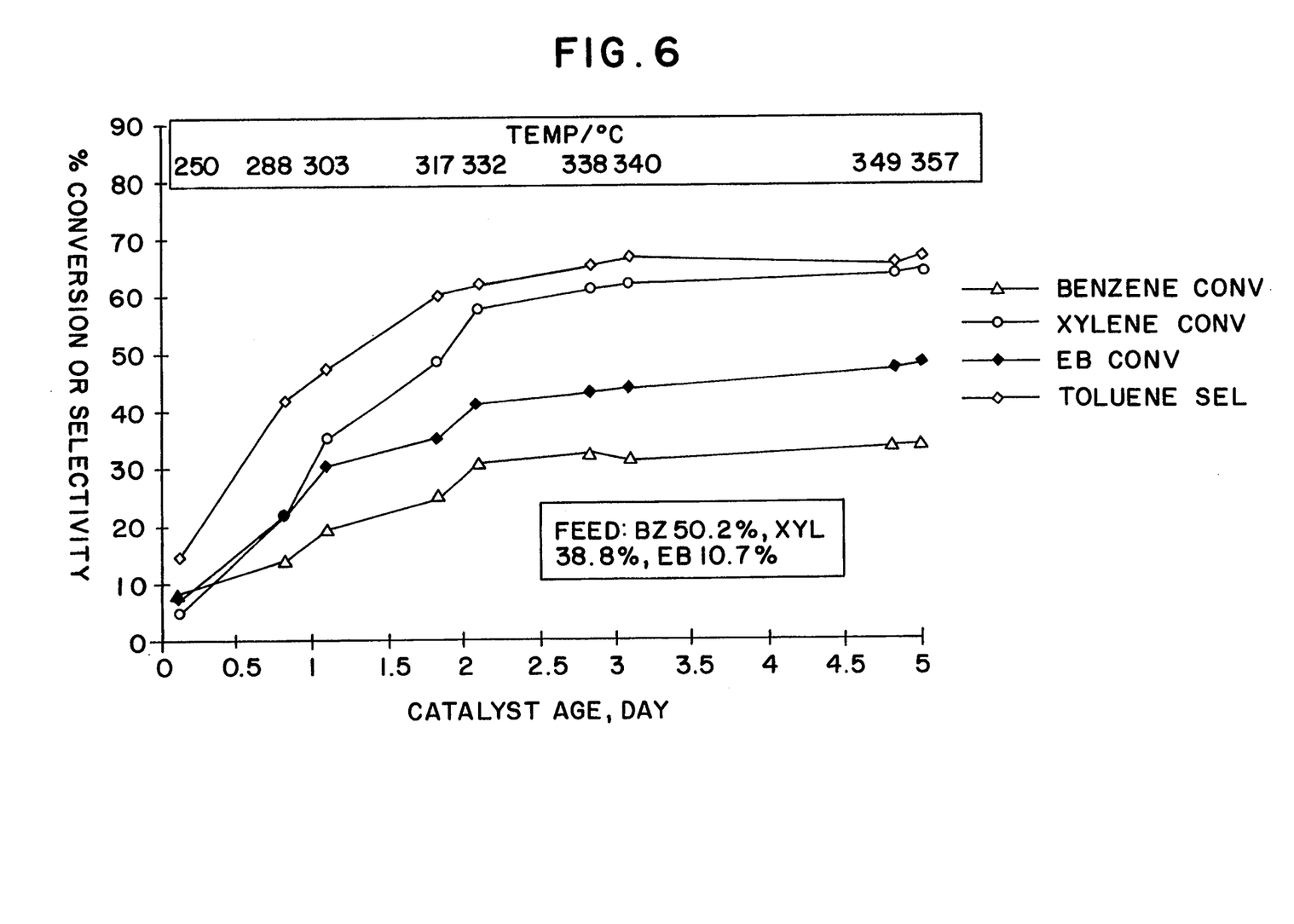

CATALYST IV - Ni(1.4%)/Zn(0.5%)/Mordenite (See FIG. 6.)

| Temperature °C. | 250 | 288 | 303 | 317 | 332 | 340 |
|---|---|---|---|---|---|---|
| Conversion, Weight % | | | | | | |
| Benzene Conv. | 8.5 | 14.0 | 19.4 | 24.8 | 30.8 | 31.2 |
| Total Xylenes Conv. | 4.7 | 21.9 | 35.1 | 48.4 | 57.6 | 61.9 |
| Ethylbenzene Conv. | 7.1 | 21.9 | 30.3 | 35.2 | 41.2 | 43.8 |
| Selectivity, Weight % | | | | | | |
| Toluene | 14.6 | 41.9 | 47.3 | 59.9 | 61.7 | 66.3 |

CATALYST V - Zn(0.5%)/Mordenite (Not graphically depicted.)

| Temperature °C. | 297 | 297 | 245 | 390 |
|---|---|---|---|---|
| Conversion, Weight % | | | | |
| Benzene Conv. | −1.9 | −0.5 | 2.9 | 6.2 |
| Total Xylenes Conv. | 3.4 | 3.1 | 8.1 | 14.4 |
| Ethylbenzene Conv. | 4.3 | 3.9 | 8.2 | 13.6 |
| Selectivity, Weight % | | | | |
| Toluene | 6.5 | 39.9 | 41.0 | 59.6 |

Figure 7:
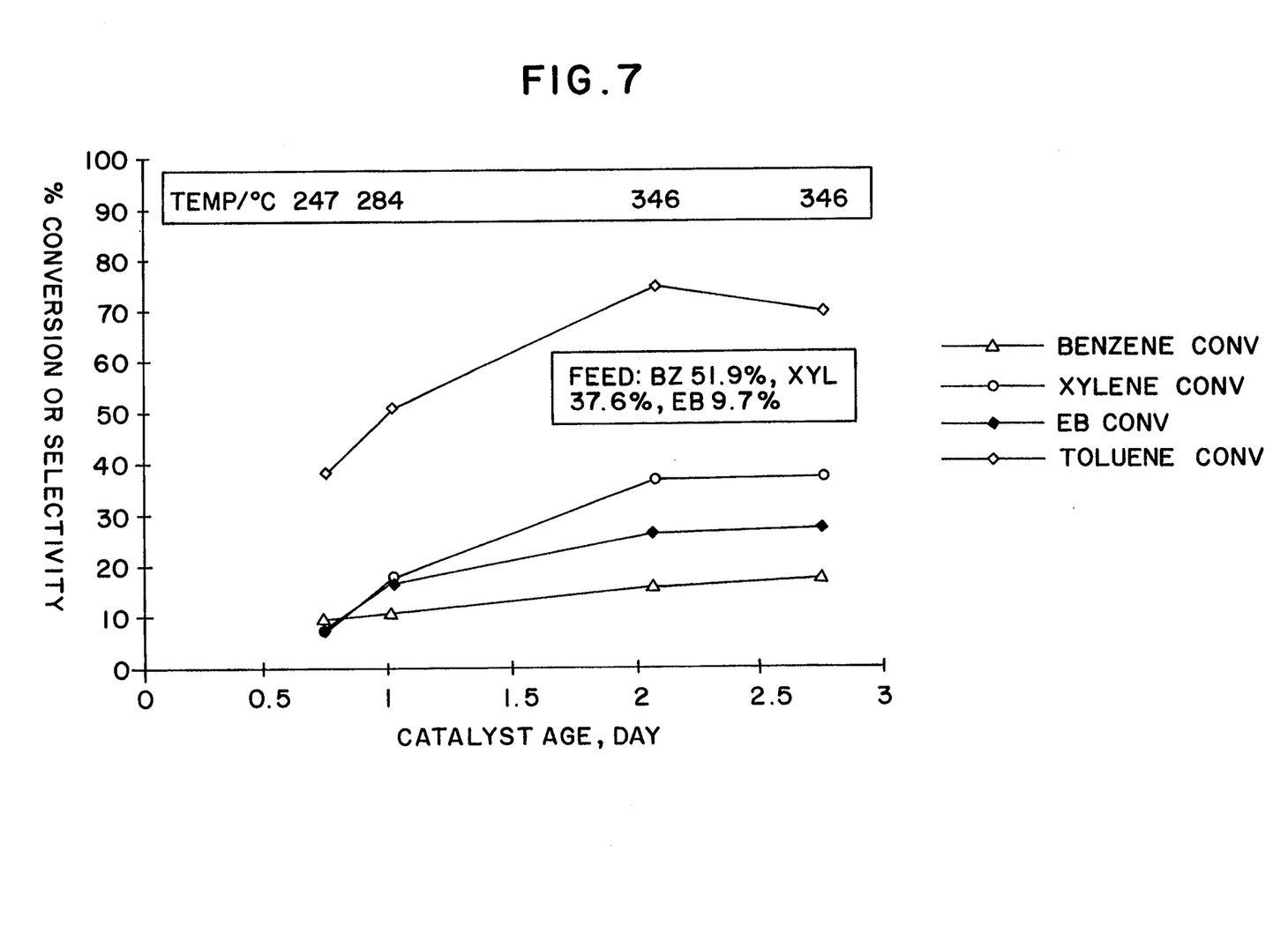
FIG. 7 is a graph depicting the relationship of the conversion of benzene, xylenes and ethylbenzene, and selectivity to toluene as a function of catalyst age over a gallium/mordenite catalyst (Catalyst VI)

CATALYST VI - Ga(0.5%)/Mordenite (See FIG. 7.)

| Temperature °C. | 247 | 284 | 346 | 346 |
|---|---|---|---|---|
| Conversion, Weight % | | | | |
| Benzene Conv. | 9.3 | 10.6 | 16.0 | 17.4 |
| Total Xylenes Conv. | 6.7 | 17.4 | 36.8 | 37.4 |
| Ethylbenzene | 7.5 | 16.5 | 26.2 | 27.4 |
| Selectivity, Weight % | | | | |
| Toluene | 38.2 | 50.9 | 74.8 | 69.8 |

CATALYST VII - Ni(0.4%)/Ga(0.4%)/Mordenite (Not graphically depicted.)

| Temperature °C. | 252 | 299 | 348 |
|---|---|---|---|
| Conversion, Weight % | | | |
| Benzene Conversion | 5.4 | 23.4 | 23.1 |
| Total Xylenes Conv. | 34.1 | 26.1 | 57.2 |
| Ethylbenzene Conv. | 28.1 | 19.2 | 39.6 |
| Selectivity, Weight % | | | |
| Toluene | 73.1 | 64.0 | 75.7 |

Figure 8:
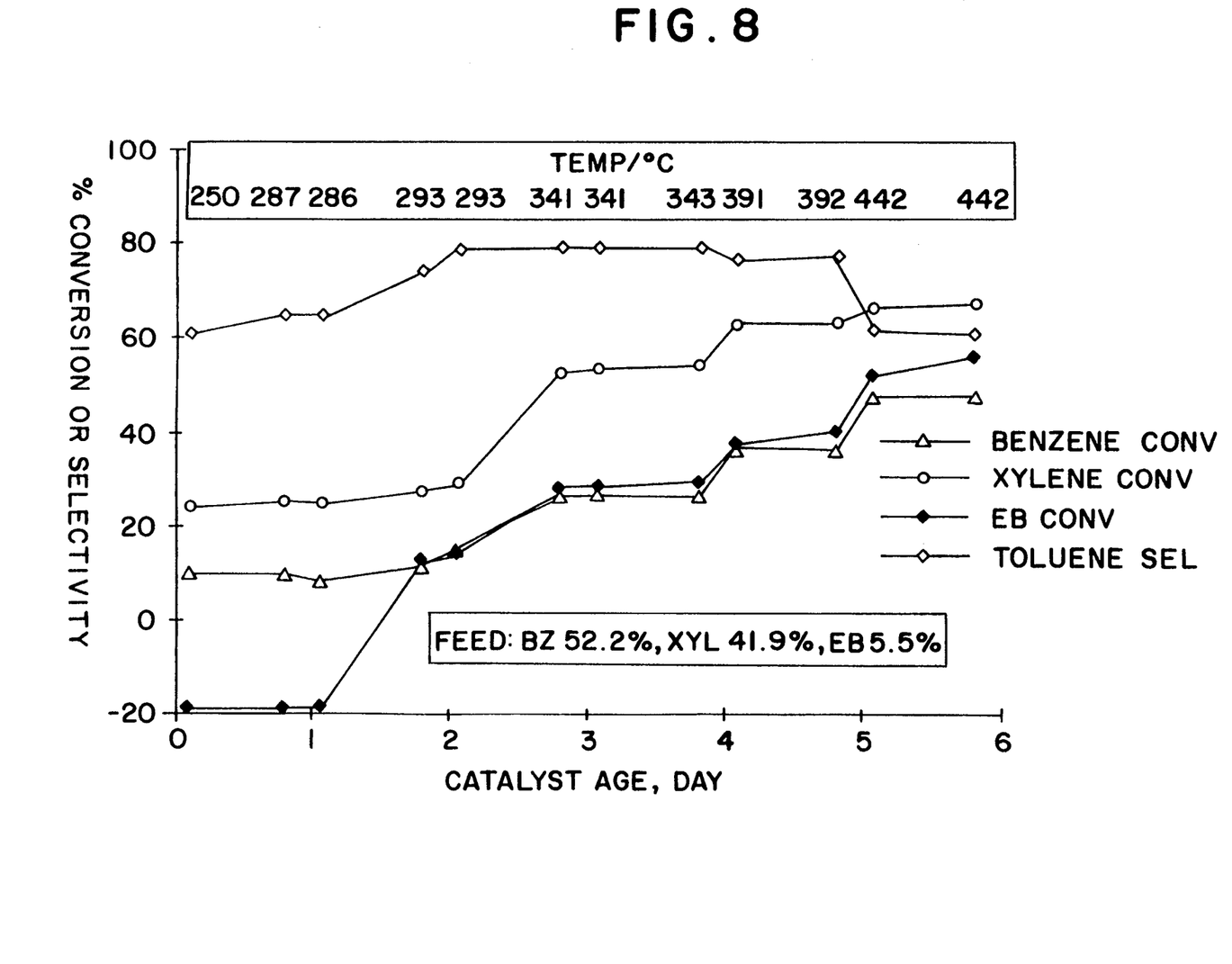
FIG. 8 is a graph depicting the relationship of the conversion of benzene, xylenes and ethylbenzene, and selectivity to toluene as a function of catalyst age over a zinc/dealuminated mordenite catalyst (Catalyst VIII).

CATALYST VIII - Zn(0.5%)/Dealuminated Mordenite (See FIG. 8.)

| Temperature °C. | 250 | 293 | 243 | 392 | 442 |
|---|---|---|---|---|---|
| Conversion, Weight % | | | | | |
| Benzene Conv. | 10.0 | 15.0 | 26.4 | 36.7 | 47.9 |
| Total Xylenes Conv. | 24.0 | 28.9 | 54.4 | 63.1 | 67.1 |
| Ethylbenzene Conv. | −18.9 | 14.0 | 29.4 | 40.0 | 56.2 |
| Selectivity, Weight % | | | | | |
| Toluene | 68.6 | 79.8 | 79.3 | 76.3 | 60.3 |

Turning again to the drawings, FIGS. 1–8 graphically illustrate the results of experimental work for those Catalysts I–IV, VI and VIII as described in TABLE 2. All tested catalysts were found to be active for the conversion of benzene, xylenes, and ethylbenzene. FIGS. 3–8 specifically depict conversion activities and selectivities over various combinations of metal-promoted mordenite catalysts (nickel, zinc and gallium and combinations of zinc and nickel and of gallium and nickel).

Catalysts I and II represent the nickel-promoted mordenite catalysts. Catalyst I, a commercially available catalyst having a nickel content of approximately 1.4 weight percent, exhibited the most favorable conversion activity as compared to all other tested catalysts, with good toluene selectivity. Depending on specific economic factors with respect to the feed mixture components and conversion products, Catalyst I can be considered one of the most effective catalysts to be used in the claimed process. Catalyst II, having a nickel content of approximately 0.5 weight percent, showed good conversion activity with higher toluene selectivity than that observed for Catalyst I, 68.1% versus 58.8%. While toluene selectivity was better for Catalyst II, the overall numbers indicate that Catalyst I outperformed Catalyst II.

As previously described, Catalyst III through VIii represented the mordenite promoted with zinc or gallium, with and without the inclusion of nickel. Catalysts III, IV and VII, included nickel and zinc or gallium, while Catalysts V, VI and VIII included only zinc or gallium. Catalysts III and IV included a combination of nickel and zinc and tested the effect of inclusion of zinc in the catalyst system. Catalyst III had nickel and zinc contents of approximately 0.3 weight percent each. As compared to Catalyst II, Catalyst III showed higher activity for xylenes and ethylbenzene conversion with slightly better selectivity to toluene than Catalyst II, which did not include zinc. These results for Catalyst III suggest that the inclusion of zinc in a nickel/mordenite catalyst system enhances the activity for xylenes and ethylbenzene conversion and improves selectivity to toluene. Increasing the amount of both nickel and zinc, however, as represented by Catalyst IV having a nickel content of 1.4 weight percent and a zinc content of 0.5 weight percent, did not affect conversion activity, but did appreciably decrease toluene selectivity. While Catalyst VII, having nickel and gallium contents of 0.4 weight percent showed good conversion activity, overall conversion activity was each poorer than the nickel/mordenite or nickel/zinc/mordenite catalysts.

Catalysts V, VI, and VIII did not include nickel. Catalyst V, having a zinc content of approximately 0.5 weight percent, showed very poor performance. Catalyst VI, having a gallium content of approximately 0.5 weight percent, and Catalyst VIII, a dealuminated mordenite having a zinc content of approximately 0.5 weight percent, showed conversion activities better than those recorded for Catalyst V, but lower than those catalysts having some nickel content. Accordingly, these results suggest the desirability of a nickel-promoted mordenite catalyst, alone or in combination with other metals.

Generally, it was observed that conversion and selectivity maintained favorable levels at temperatures around 300° C. While in some instances, conversion activity and selectivity to toluene values were higher at temperatures greater than 300° C., it is well known that lower temperatures prolong the life of the catalyst. Accordingly, appreciable increases in conversion/selectivity due to increases in temperature are often offset by shortened catalyst life. Summary results listing conversion activities for benzene, xylenes, ethylbenzene and selectivity to toluene at a temperature around 300° C. are summarized in TABLE 3.

TABLE 3

Summary Results for Conversion Activities of Benzene, Xylenes and Ethylbenzene (EB) and Toluene Selectivities.

| | Catalyst | Temp., °C. | Total Xylenes | EB | Benzene | % Selectivity to toluene | Represented in FIG. |
|---|---|---|---|---|---|---|---|
| I | Ni(1.4%)/Mordenite (SAR = 18) | 301 | 51.5 | 40.1 | 25.2 | 58.8 | 1,2,3 |
| II | Ni(0.5%)/Mordenite (SAR = 18) | 300 | 29.22 | 22.70 | 14.01 | 68.1 | 4 |
| III | Ni(0.3%)/Zn(0.3%)/Mord (SAR = 18) | 298 | 37.06 | 26.87 | 14.62 | 73.79 | 5 |
| IV | Ni(1.4%)/Zn(0.5%)/Mord (SAR = 18) | 303 | 35.2 | 30.3 | 19.45 | 47.25 | 6 |
| V | Zn(0.5%)/Mord (SAR = 17) | 297 | 3.3 | 3.9 | −0.5 | 39.93 | — |
| VI | Ga(0.5%)/Mord (SAR = 18) | 284 | 17.4 | 16.5 | 10.62 | 50.9 | 7 |
| VII | Ni(0.4%)/Ga(0.4%)/Mord (SAR = 18) | 299 | 26.10 | 19.2 | 23.40 | 63.98 | — |
| VIII | Zn/Dealuminated Mord (SAR = 59) | 293 | 28.9 | 14.0 | 15.1 | 79.0 | 8 |

In summary, and as can be seen in TABLE 3, Catalyst I exhibited the most favorable conversions of benzene, xylene(s) and ethylbenzene with good toluene selectivity. Catalysts II–IV also exhibited good conversion percentages, with high percent selectivity to toluene. Depending on the economic forces shaping the benzene/toluene markets, each of Catalysts I–IV could be used in an efficient process for the conversion of mixed alkylaromatic feedstock mixtures, including benzene, xylenes and ethylbenzene, to hydrocarbons components comprising primarily toluene. While the results depicted in TABLE 3 were recorded for temperatures of approximately 300° C., higher temperatures (refer to Table 2) may be appropriate as a function of the catalyst employed in the conversion reaction.

While the invention has been described with reference to particular embodiments thereof, it will be apparent to those skilled in the art that various changes and modifications can be made without departing from the spirit of the invention or from the scope of the appended claims.

What is claimed is:

1. A process for the conversion of aromatic hydrocarbons including benzene, xylene(s) and ethylbenzene to hydrocarbon components comprising primarily toluene, the steps comprising:
   (a) establishing a catalyst reaction zone having a metal-loaded mordenite zeolite catalyst, said metal selected from the group consisting of zinc, gallium, a combination of zinc and nickel, or a combination of gallium and nickel;
   (b) introducing into said reaction zone a mixed feedstock of aromatic hydrocarbons comprising benzene and xylene(s);

(c) contacting said feedstock with said metal-loaded mordenite catalyst;

(d) operating the reaction zone under temperature and pressure conditions to effect the conversion of said feedstock to hydrocarbon components containing primarily toluene; and (e) recovering the conversion product containing toluene from the reaction zone.

2. The process of claim 1, wherein said mixed feedstock is introduced at a rate sufficient to provide a liquid hourly space velocity of approximately 2 hour$^{-1}$.

3. The process of claim 1, wherein contemporaneously with said feedstock, hydrogen is introduced into said reaction zone as a cofeed in an amount to provide a hydrogen/feedstock mole ratio within the range of 3:1 to 4:1.

4. The process of claim 1, wherein said reaction zone is operated at a temperature within the range of 250° to 450° C. and at a pressure within the range of 500 to 700 psig.

5. The process of claim 1, wherein said metal-loaded mordenite exhibits a silica to alumina mole ratio of about 18 and is modified by the inclusion of amounts of nickel and zinc having a concentration of at least 0.3 weight percent nickel and at least 0.3 weight percent zinc.

6. The process of claim 1, wherein said metal-loaded mordenite exhibits a silica to alumina mole ratio of about 18 and is modified by the inclusion of nickel and zinc having a concentration of approximately 1.4 weight percent nickel and approximately 0.5 weight percent zinc.

7. The process of claim 1, wherein said metal-loaded mordenite exhibits a silica to alumina molar ratio of about 18 and is modified by the inclusion of gallium having a concentration of approximately 0.5 weight percent.

8. The process of claim 1, wherein said metal-loaded mordenite is modified by the inclusion of gallium and nickel, each having a concentration of approximately 0.4 weight percent.

9. The process of claim 1, wherein said metal-loaded mordenite exhibits a silica to alumina molar ratio of 59 and is modified by the inclusion of zinc having a concentration of approximately 0.5 weight percent.

10. The process of claim 1, wherein said feedstock supplied to said reaction zone contains ethylbenzene in a concentration within the range of 5 to 11 weight percent.

11. The process according to claim 1, wherein said conversion product recovered from said reaction zone exhibits a weight percent selectivity to toluene greater than 40 percent.

12. The process according to claim 5, wherein said conversion product recovered from said reaction zone exhibits a weight percent selectivity to toluene greater than 70 percent.

13. The process according to claim 9, wherein said conversion product recovered from said reaction zone exhibits a weight percent selectivity to toluene greater than 75 percent.

* * * * *